United States Patent [19]

Smith, Jr. et al.

[11] Patent Number: 5,122,236

[45] Date of Patent: Jun. 16, 1992

[54] METHOD FOR REMOVAL OF DIMETHYL ETHER AND METHANOL FROM $C_4$ HYDROCARBON STREAMS

[76] Inventors: Lawrence A. Smith, Jr.; Edward M. Jones, Jr.; Dennis Hearn, all of P.O. Box 890509, Houston, Tex. 77289-0509

[21] Appl. No.: 526,458

[22] Filed: May 21, 1990

[51] Int. Cl.$^5$ .................. B01D 3/34; C07C 7/10
[52] U.S. Cl. .................. 203/43; 203/45; 203/77; 203/88; 203/92; 568/697; 568/699; 585/802; 585/833; 585/840; 585/867
[58] Field of Search .................. 203/44, 45, 46, 92, 203/95, 88, 74, 76, 77, 43; 585/802, 809, 833, 835, 840, 867; 568/699, 697

[56] References Cited

U.S. PATENT DOCUMENTS

| | | | |
|---|---|---|---|
| 3,121,124 | 2/1964 | Verdol | 260/677 |
| 3,170,000 | 2/1965 | Verdol | 260/677 |
| 3,270,081 | 8/1966 | Verdol | 260/681 |
| 3,629,478 | 8/1969 | Haunschild | 260/677 A |
| 3,634,534 | 8/1969 | Haunschild | 260/677 A |
| 4,018,843 | 4/1977 | Machaux et al. | 585/809 |
| 4,071,567 | 1/1978 | Anallotti et al. | 260/614 A |
| 4,144,138 | 3/1979 | Rao et al. | 203/46 |
| 4,218,569 | 8/1980 | Chase et al. | 585/832 |
| 4,302,298 | 11/1981 | Mikitenko et al. | 203/93 |
| 4,307,254 | 12/1981 | Smith, Jr. | 568/697 |
| 4,334,964 | 6/1982 | Prezeli et al. | 203/85 |
| 4,465,870 | 8/1984 | Huskovits | 568/697 |
| 4,479,018 | 10/1984 | Van Pool | 585/723 |
| 4,575,366 | 3/1986 | Vora | 568/697 |
| 4,575,567 | 3/1986 | Vora | 568/697 |
| 4,603,225 | 7/1986 | Colaiane et al. | 568/697 |
| 4,814,517 | 3/1989 | Trubac | 568/679 |

Primary Examiner—Wilbur Bascomb, Jr.
Attorney, Agent, or Firm—Kenneth H. Johnson

[57] ABSTRACT

A process for removing dimethyl ether (DME) and methanol impurities from $C_4$ hydrocarbon stream without substantial loss of $C_4$ hydrocarbons by fractionating a $C_4$ hydrocarbon stream containing DME and methanol at low levels, e.g., less than 5 wt. % to produce an overhead of about 20 to 40 volume % of the $C_4$ stream, condensing the overhead, contacting the condensed overhead with about 1 to 5 volumes of water, thereby removing a portion of the DME and methanol from the $C_4$ stream, returning substantially all of the $C_4$ stream, except the small amount solubilized in the water, to the fractionation and flashing the solubilized DME and hydrocarbons from the water. The fractionation and extraction are preferably carried out at elevated pressures, e.g., 200 to 300 psig to avoid refrigeration of the overhead condensation. The flashing of the DME and hydrocarbons is carried out by reducing the pressure on the water, e.g. atmospheric pressure at a temperature in the range of 20° C. to 50° C., leaving methanol in the water. The methanol can be removed by distillation or by contacting the methanol containing water stream with a large volume of a $C_4$ stream whereby a portion of the methanol is extracted in the $C_4$ stream. The methanol depleted stream can recycle to contact the condensed overhead from the fractionation thereby establishing a closed circuit water wash/methanol recovery system.

16 Claims, 1 Drawing Sheet

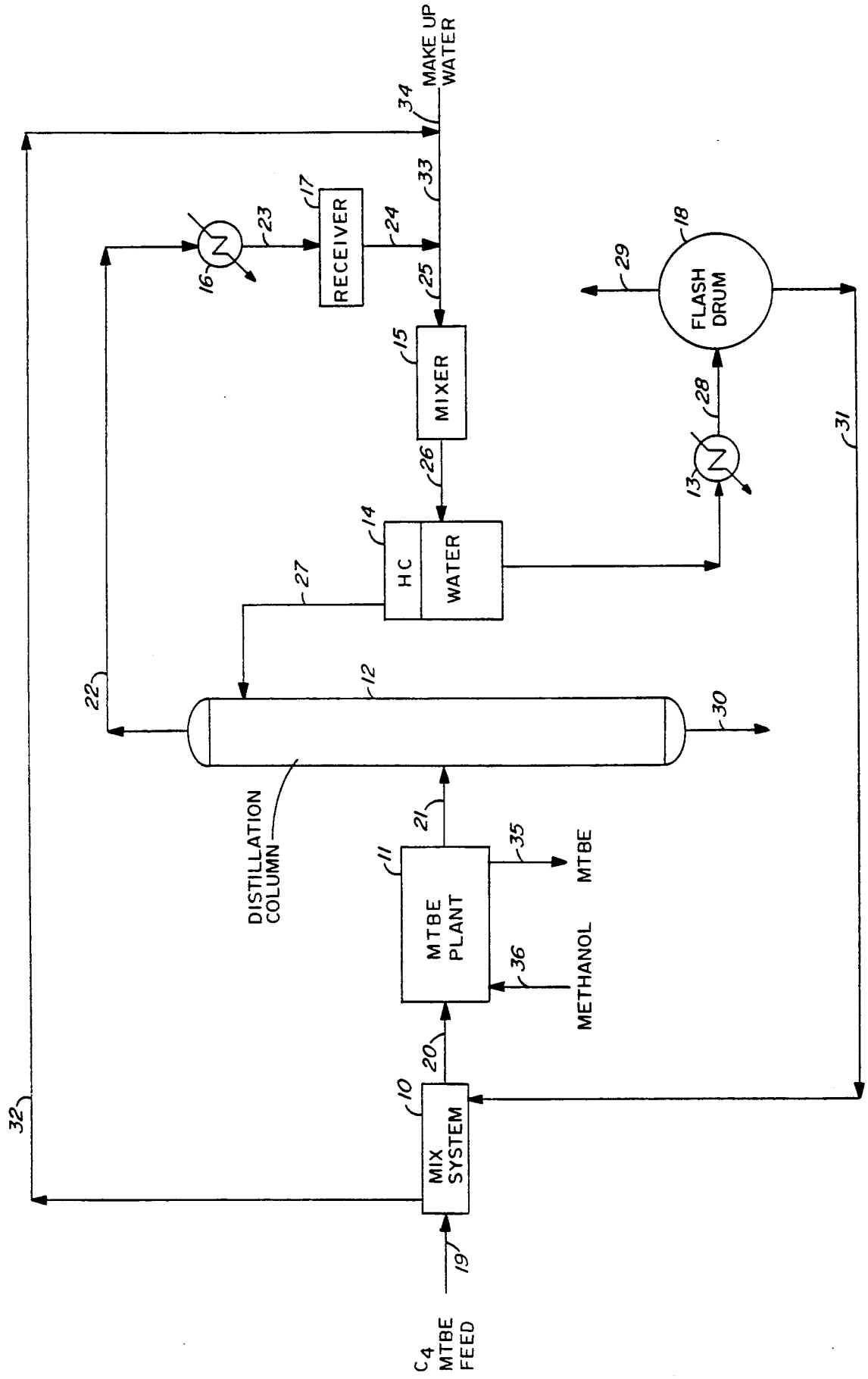

METHOD FOR REMOVAL OF DIMETHYL ETHER AND METHANOL FROM C₄ HYDROCARBON STREAMS

BACKGROUND OF THE INVENTION

1. Field of the Invention

The present invention relates to a process for the removal of dimethyl ether and/or methanol from C4 hydrocarbon streams.

2. Related Art

The production of methyl tertiary butyl ether (MTBE) is usually carried out by selectively reacting isobutene contained in a refinery $C_4$ stream with methanol in the presence of an acid catalyst. The resulting MTBE product is separated from the $C_4$ stream which is then potentially useful for other purposes such as alkylation. However the $C_4$ stream will contain dimethyl ether (DME) and/or methanol in small amounts generally from 10 to 50 ppm up to several thousand parts per million. The precise contaminant and its amount will vary somewhat depending on the specific MTBE process employed.

The separation of MTBE from the hydrocarbon product stream is not a problem because of the boiling point difference between MTBE and $C_4$, the DME and methanol are lower boiling and contaminate the $C_4$ fraction.

In acid alkylations the presence of DME causes at the least the use of more acid than the alkylation per se. In the case of sulfuric acid alkylations this may be a tolerable detriment, however, in the case of HF alkylations an acid soluble oil is formed which interferes with the separation of the alkylate product from the acid and may lead to fouling of the alkylation unit.

The removal of methanol can be carried out with a water wash system since methanol is relatively soluble in water, however, conventional water wash systems when used to treat the entire residual hydrocarbon stream do not remove the major portion of the dimethyl ether. In order to remove the DME to acceptable levels, the example for alkylation, would require a volume of water equal to about three times the volume of the hydrocarbon stream being treated. Hence, a large volume of waste water would be produced, which in addition to DME would contain large amounts of hydrocarbon. Handling this volume of waste water treatment makes the conventional water wash unattractive.

The present process provides for the removal of DME and methanol to satisfactorily low levels while using very low volumes of treatment water. In one embodiment a close water wash system which substantially eliminates waste water disposal is employed. These and other features and advantages will become apparent from the following description.

SUMMARY OF THE INVENTION

Briefly the present invention is a process for removing DME, methanol or mixtures thereof from a $C_4$ hydrocarbon stream comprising (a) feeding a $C_4$ hydrocarbon feed stream containing DME, methanol or a mixture thereof to a distillation column, (b) fractionating the feed stream in said distillation column to provide a vaporous hydrocarbon overhead fraction comprising from about 25 to 40 volume percent of said feed stream, preferably about 25 to 35 volume percent of said feed stream and a bottoms fraction having a substantially lower amount of DME, methanol or mixture thereof than said feed stream, (c) condensing the vaporous hydrocarbon overhead fraction, (d) contacting said condensed hydrocarbon overhead fraction with from about 0.05 to 5 volumes of water based on the condensed hydrocarbon overhead fraction, (e) separating the condensed hydrocarbon fraction from the water (f) returning the condensed hydrocarbon overhead fraction to the distillation column and recovering the water from step (e). What has happened in the process described above is that the DME and/or methanol was concentrated in the overhead, the bottoms being substantially free of these contaminants, the DME and/or methanol was extracted from the condensed overhead fraction with water to remove a substantial portion of the DME and/or methanol therefrom and the major portion of the overhead returned to the column, i.e., substantially a full reflux of the overhead, since very little hydrocarbon is lost in water extraction.

In a further embodiment the water from the extraction is passed to a flash drum where DME and hydrocarbons are flashed out and only methanol remains in water. This stream can be fractionated to recover methanol but in a preferred embodiment the methanol containing water stream is contacted with an isobutene hydrocarbon feed (essentially a $C_4$ feed) going to a reactor to produce MTBE whereby a portion of the methanol is extracted from the water into the isobutene feed to the MTBE reactor and is thereby recycled to the MTBE reaction. The water leaving the MTBE feed contact is recycled to the hydrocarbon overhead fraction extraction (step d described above) where it again extracts DME and/or methanol followed by the flashing of the DME and hydrocarbon and recycle to the MTBE feed contact. Thus a substantially closed circuit water wash system is provided with only make up water as necessary being added. The DME and hydrocarbons flashed from the water are suitable for use as fuel, although further processing such as with selective molecular sieves may be carried out to remove DME and recover the hydrocarbons. DME has especial value as a none polluting aerosol propellant.

BRIEF DESCRIPTION OF THE DRAWING

The FIGURE is a schematic representation of a preferred embodiment of the present invention.

DETAILED DESCRIPTION OF THE INVENTION

The process of steps (a) through (f) may be run at any pressure. The pressure selected will then determine the temperature in the distillation column based on the constitution of the materials being fractionated in the column. Generally pressures of atmospheric through 500 psig may be used, however pressures of 200–300 psig are preferred in order to avoid refrigeration in step (c) i.e., condensing the hydrocarbon overhead fraction of a $C_4$ stream. A typical $C_4$ stream in the process at 250 psig has an overhead temperature of about 100° C. (representing the lowest boiling material).

Step (a)

The hydrocarbon feed to the distillation column is the residual stream from an MTBE process, or any other process which will leave DME and/or methanol as impurities usually in amounts of 5 weight percent or less. Such streams used for producing MTBE are mixed $C_4$ streams containing principally isobutane (E-$C_4$), normal butane (n-C$_4$) butene (B-1), isobutene (I-B), trans butene-2 (TB-2) and cis butene-2 (CB-2) (plus some minor impurities including butadiene, C$_3$'s and C$_5$'s). The C$_4$ hydrocarbon feed stream in the present process is substantially the same stream with a reduced amount of isobutene from MTBE manufacture and the DME and methanol impurities. There are several processes for producing MTBE for example U.S. Pat. Nos. 3,121.124; 3,270,081; 3,170,000; 3,629,478, 3,634,534; 4,071,567 and 4,307,254; and the feed streams vary in the specific ratios of C$_4$, e.g. isobutene may vary from about 5 to 60 wt.% of the MTBE feed. Also the degree of isobutene conversion varies in the processes, but are generally operated commercially to obtain 85%+ conversion. The DME and methanol may comprise up to 5 wt.% of the stream once the MTBE is removed, but usually they would constitute less than 1 wt.% of the residual C$_4$ stream.

The location of the feed into the distillation column of the present invention is not critical, but is preferable to have the feed into the middle portion of the column.

Step (b)

The distillation column is preferably operated at 200 to 300 psig and the temperature in the overhead is that of the lowest boiling component at the pressure employed. However, because of the closeness of the boiling points of the C$_4$'s in the feed to the column the overhead composition will comprise all the C$_4$ components. albeit in somewhat different ratios than the feed. The DME and methanol being the lowest boiling components (also any C$_3$'s) are substantially all in the overhead. The DME and/or methanol in the bottoms is less than 10 parts per million. The amount of overhead taken is from about 25 to 40% of the feed, preferably about 25 to 35% of the feed. This concentrates the DME and/or methanol to about 4 to 6% of the hydrocarbon overhead fraction. The amount of the DME and methanol can vary widely from this range depending on their level in the feed coming into the column, e.g., if the DME and methanol comprised 2 wt.% of the feed, substantially all of this amount would be in a 30% overhead and would comprise about 6% of the vaporous overhead.

Step (c)

The hydrocarbon overhead fraction is condensed in order to provide a liquid fraction for contact with water in Step (d). The overhead is also cooled to 20° C. to 50° C. At the preferred pressures, i.e., 200-300 psig the condensation is obtained with ambient temperature water (e.g., up to 30° C. in summer) without refrigeration. The condensed overhead is also cooled with the water. The temperature of the overhead is important for water contact since lower temperatures favor the solubility of DME in the water.

Step (d)

The condensed hydrocarbon overhead fraction is then contacted with a water stream at 20° to 50° C. The pressure is preferably in the 200-300 psig range. In any event the pressure must be sufficient to maintain the DME in the water phase. The water can be fresh or may contain some methanol and/or hydrocarbon as will be explained later. The water is employed in a range of 0.05 to 5 volumes based on the volume of condensed hydrocarbon overhead it is contacting, preferably at least a 0.05:1 volume ratio of water to hydrocarbon will be employed. The water and hydrocarbon are intimately mixed in an appropriate mixing apparatus at a temperature in the range of 20° C. to 50° C. and passed to a decanter or other separator means.

Step (e)

The water and hydrocarbon phases are separated in the decanter and are continuously removed. The water is enriched in DME, methanol and hydrocarbons to the limit of their solubility. The pressure is preferably in the range of 200 to 300 psig. Very little of the hydrocarbon is soluble in water and essentially 100% is returned to the distillation column.

Step (f)

The water leaving the decanter has extracted and amount of DME equal to or greater than the amount produced in the production of MTBE along with a high percentage of methanol. In a preferred embodiment the water is heated and passed to flash drums operated at a lower pressure than the 200-300 psig of the system. Preferably the pressure is atmospheric. The DME and any solubilized hydrocarbons are vaporized at atmospheric pressure and the 20° C. to 50° C. temperature of the water. This is not a large stream, hence the simplest manner to handle these two materials is to burn the stream as fuel. However, they may be separated and recovered.

The water with DME and hydrocarbons substantially removed can be fractionated to remove and recover methanol and the methanol removed can then be recycled to the MTBE feed and a substantially closed circuit established for the water wash. However, there is energy consumed in the water distillation and in a preferred embodiment this energy consumption is eliminated.

In the preferred embodiment the water stream containing the methanol removed from the hydrocarbon overhead fraction is contacted with an MTBE C$_4$ feed prior to its entry into a reactor. This is an advantage if the C$_4$ stream is to be employed in a process where methanol is a reactant such as the reaction of isobutene with methanol to produce MTBE. In this case a relatively large volume of C$_4$ feed is contacted with a small volume of water (ratio of hydrocarbon: water is in the range of 1 to 10 or more e.g. 20:1). The mass transfer effect is to desorb the methanol from the water into the C$_4$ feed where it is utilized along with other added methanol in the MTBE reaction. The water is recovered, depleted in methanol and recycled to the contact with liquid hydrocarbon overhead in step (d). Thus, the essentially closed circuit water wash is established without a substantial energy requirement.

The incoming MTBE C$_4$ feed is generally at a temperature of 20°-40° C. at pressures of 70 to 200 psig, however, it need not be since neither the temperature not the pressure are critical so long as they generally fall in the ranges of 0° C. to 80° C. and pressures in the range of atmospheric to 300 psig and the MTBE feed is in liquid phase under those conditions.

Referring now to the FIGURE, a more preferred embodiment as described is illustrated in schematic form. Such elements as reboilers, valves, compressors, etc. have been omitted, but the appropriate insertion in normal engineering practice would be obvious expedients. In this embodiment the C$_4$ hydrocarbon feedstream 21 is that produced by the reaction of methanol with isobutene in the C$_4$ MTBE feed to produce MTBE. The compositions of the various streams are shown in the TABLE (major components or those relevant to the present invention). For the purposes of this illustration the MTBE process is that described in U.S. Pat. No. 4,307,254 which is incorporated herein. The $C_4$ hydrocarbon feed stream 21 is fed near the middle of distillation column 12 (which for the purpose of this illustration is a 24 tray column) operated at 250 psig. The $C_4$ hydrocarbon overhead fraction 22 has a temperature of about 100° C. The vaporous stream 22 passes through condenser 16 (also operated at 250 psig) where it is condensed and cooled to about 40° C. and collected via 23 in receiver 17 (at 250 psig). The liquid $C_4$ hydrocarbon fraction passes via 24 and 25 where a feed of recycle water/methanol (0.05:1 volume ratio of recycle water to hydrocarbon) joins it from line 33 and passes to mixer 15 for intimate contact of the two phases at 250 psig. Note the two streams could be added by separate lines to the mixer, but more contact is obtained in this fashion. From the mixer the two phases pass via 26 to a decanter 14 where the phases separate at 250 psig. The hydrocarbon phase, now having a reduced DME and methanol content compared to that in line 22 passes through line 27 back to distillation tower 12 as reflux.

The water phase enriched in DME, methanol and some hydrocarbons passes via line 28 to flash drum 18 operated at atmospheric pressure. A heater 13 may be positioned in line 28 to provide supplemental heat for the flash drum. The DME and hydrocarbons are essentially all volatilized and removed as vapor through line 29.

The water enriched in methanol in liquid phase passes from the flash drum via line 31 to the mixing system 10, which may consist of a mixer (not shown) and decanter (not shown) as previously described, a counterflow contact tower or the like, where $C_4$ MTBE feed 19 contacts the water in a hydrocarbon:water extract ratio of 10:1 and extracts methanol therefrom. The methanol depleted water passes from the mix system 10 via 32 whence to line 33 for recycle into the mixer 15. A line 34 is provided for make up water.

The bottoms 30 from distillation column 12 are substantially free of DME and methanol and may be recovered for further use. The $C_4$ MTBE feed containing methanol extracted from the water 31 leaves the mix system 10 via 20 to the MTBE plant 11 where additional methanol 36 is added to react with the isobutene to produce MTBE 35 which is separated and recovered for use, for example, as a gasoline octane improver and the unreacted components of the $C_4$ MTBE feed are recovered as stream 21 as feed to the distillation column 12.

The invention claimed is:

1. A process for removing dimethyl ether, methanol or mixture thereof from a $C_4$ hydrocarbon stream comprising:

(a) feeding a $C_4$ hydrocarbon feed stream containing dimethyl ether, methanol or mixture thereof to a distillation column,
    (b) fractionating the feed stream in said distillation column to provide a vaporous hydrocarbon overhead fraction comprising from about 20 to 40 volume percent of said feed stream and a bottoms fraction containing a substantially lower amount of dimethyl ether, methanol or mixture thereof than said feed stream,
    (c) condensing the vaporous hydrocarbon overhead fraction to form a liquid hydrocarbon overhead fraction,
    (d) contacting the liquid hydrocarbon overhead fraction with from about 0.05 to 5 volumes of water per volume of liquid hydrocarbon overhead fraction,
    (e) separating the liquid hydrocarbon overhead fraction from the water,
    (f) returning the liquid hydrocarbon overhead fraction to said distillation column, and
    (g) recovering said water from step (e).

2. The process according to claim 1 wherein steps (a) through (f) are operated at a pressure in the range of 200 to 300 psig.

3. The process according to claim 2 wherein said vaporous hydrocarbon overhead fraction of step (b) comprises about 25 to 35 volume percent of said feed stream.

4. The process according to claim 2 wherein said liquid hydrocarbon overhead fraction is at a temperature in the range of 20° C. to 50° C.

5. The process according to claim 2 wherein the liquid hydrocarbon overhead fraction and said water are intimately mixed.

6. The process according to claim 5 wherein at least one volume of water per 15 volumes of liquid hydrocarbon overhead fraction in step (d) is present.

7. The process according to claim 6 wherein the liquid hydrocarbon fraction of step (f) contains less dimethyl ether, methanol or mixture thereof than said vaporous hydrocarbon overhead fraction of step (b).

8. The process according to claim 7 wherein said liquid hydrocarbon overhead fraction of step (f) comprises substantially all of the hydrocarbons of said vaporous hydrocarbon overhead fraction of step (b).

9. The process according to claim 1 wherein said vaporous hydrocarbon overhead fraction contains dimethyl ether.

10. The process according to claim 1 wherein said vaporous hydrocarbon overhead fraction contains methanol.

11. The process according to claim 1 wherein said vaporous hydrocarbon overhead fraction contains dimethyl ether and methanol.

12. A process for removing dimethyl ether, methanol or mixture thereof from a $C_4$ hydrocarbon stream comprising:

TABLE

| Component Lbs/hr | STREAM | | | | | | | | |
|---|---|---|---|---|---|---|---|---|---|
|  | 19 | 20 21 | 22-24 | 27 | 28 | 30 | 31 | 32 | 33 |
| Isobutene | 21,421 | 21,421 | 321 | 320.5 |  | 535.5 | — | — | — |
| Other $C_4$ (includes $C_3$ and $C_5$) | 97,987 | 97,987 | 37,165 | 37,129 | 36 | 97,935 | — | — | — |
| Methanol | — | 1,356 | 2,292 | 621.9 | 6,199 | — | 5,885 | 4,529 | 4,529 |
| DME | — | 0.4 | 178 | 159.4 | 18.7 | — | 0.5 | 0.02 | 0.02 |
| Water | — | 47.8 | 15 | 15 | 4,985 | — | 4,647 | 4,599 | 5,000 |

(a) feeding a $C_4$ hydrocarbon feed stream containing at least methanol as an impurity to a distillation column, (b) fractionating the feed stream in said distillation column to provide a vaporous overhead fraction comprising from about 20 to 40 volume percent of said feed stream and containing a substantially greater amount of methanol than said feed stream, and a bottoms fraction containing a substantially lower amount of methanol than said feed stream, (c) condensing the vaporous hydrocarbon overhead fraction to form a liquid hydrocarbon overhead fraction, (d) contacting the liquid hydrocarbon overhead fraction with from about 0.05 to 5 volumes of water per volume of liquid hydrocarbon overhead fraction, whereby a portion of the methanol is extracted from said liquid hydrocarbon fraction into said water, (e) separating the liquid hydrocarbon overhead fraction from the water, (f) returning the liquid hydrocarbon overhead fraction to the distillation column, (g) recovering said water from step (e), and (h) contacting said water with a $C_4$ hydrocarbon methyl tertiary butyl ether stream in a volume ratio of $C_4$ hydrocarbon: water in the range of 1 to 20:1 whereby a portion of said methanol is extracted from said water into said $C_4$ hydrocarbon methyl tertiary butyl ether stream.

13. The process according to claim 12 wherein said water from step (h) is recovered and recycled to step (d).

14. The process according to claim 13 wherein dimethyl ether is also present in said $C_4$ hydrocarbon feed stream as an impurity.

15. A process for removing dimethyl ether and methanol from a $C_4$ hydrocarbon feed stream comprising:

(a) feeding a $C_4$ hydrocarbon stream containing dimethyl ether and methanol as impurities to a distillation column, (b) fractionating the feed stream in said distillation column to provide a vaporous overhead comprising from about 20 to 40 volume percent of said feed stream and containing a substantially greater amount of dimethyl ether and methanol than said feed stream, and a bottoms fraction containing a substantially lower amount of dimethyl ether and methanol than said feed stream, (c) condensing the vaporous hydrocarbon overhead fraction to form a liquid hydrocarbon overhead fraction and cooling said liquid hydrocarbon overhead fraction to a temperature in the range of 20° C. to 50° C., (d) intimately contacting said liquid hydrocarbon overhead fraction with from about 1 to 5 volumes of water per volume of said liquid hydrocarbon at a temperature in the range of 20° C. to 50° C., based on the volume of liquid hydrocarbon overhead fraction whereby a portion of said dimethyl ether and methanol is extracted from said liquid hydrocarbon overhead fraction into said water, (e) separating said liquid hydrocarbon overhead fraction from said water, (f) returning said liquid hydrocarbon overhead fraction to the distillation column, (g) recovering said water from step (e), and (h) passing said recovered water to a zone of reduced pressure wherein dimethyl ether and any hydrocarbons solubilized in said water are volatilized from said water, said steps (b) through (f) being conducted at a pressure in the range of 200 to 300 psig and step (h) at a pressure sufficiently low to volatilize substantially all of said dimethyl ether at the temperature of said water, said water containing a substantial portion of said methanol extracted from said liquid hydrocarbon overhead fraction.

16. The process according to claim 15 wherein water is recovered from step (h) and contacted with a $C_4$ hydrocarbon methyl tertiary butyl ether stream in a volume ration of $C_4$ hydrocarbon: water in the range of 1 to 20:1 whereby a portion of said methanol is extracted from said water into said $C_4$ hydrocarbon methyl tertiary butyl ether stream and said water stream is recovered from said contacting with said $C_4$ hydrocarbon methyl tertiary butyl either stream and recycled to step (d).

* * * * *